United States Patent
Peiler et al.

[11] Patent Number: 5,769,813
[45] Date of Patent: Jun. 23, 1998

[54] INDICATOR TAMPON APPLICATOR

[76] Inventors: Frances K. Peiler, 45-850 G1 Luana Pl., Kaneohe, Hi. 96744; Larisa H. Peiler, 40 Givens Ave., Stamford, Conn. 06902

[21] Appl. No.: 728,187

[22] Filed: Oct. 9, 1996

Related U.S. Application Data

[63] Continuation-in-part of Ser. No. 477,401, Jun. 7, 1995, abandoned.

[51] Int. Cl.$^6$ .................................................. A61F 13/20
[52] U.S. Cl. ............................................. 604/11; 604/285
[58] Field of Search ........................... 604/11–18, 904, 604/285

[56] References Cited

U.S. PATENT DOCUMENTS

| | | | |
|---|---|---|---|
| 2,112,021 | 3/1938 | Harris | 604/904 |
| 3,794,024 | 2/1974 | Kokx et al. | 604/904 |
| 5,273,521 | 12/1993 | Peiler et al. | 604/904 |

*Primary Examiner*—John G. Weiss
*Assistant Examiner*—Dennis Ruhl

[57] ABSTRACT

The present invention improves the conventional tampon assembly, wholly and in parts including the tampon assembly for delivery of medicament with an absorbent body having an improved rounded front-end, improved single plunger and dual, telescopic plunger members both incorporating a dosage measurement scale for medicament dosage administration; further improves the hydrophilic body of the tampon, applicator housing and plungers, inserter devices, withdrawal string and any other movable parts operating independently or sychronously. Improvement incorporates medically well known indicators for example, litmus for measuring pH balance, of various shapes, sizes or color-spectrums applied to the tampon assembly, wholly or in parts as described above by means including such as, but not limited to, impregnation within, adherence to, coated with or otherwise applied as is reasonable to maintain the integrity and sufficiency of various indicators for purposes of testing internally or externally excreted biological fluid for detection and identification of bacterium concentration levels present in said biological fluids via corresponding indicator prognosis charts. Moreover, also included in the utility of indicator application in the manufacture are generally absorbent products that utilize the same or similar hydrophilic materials as those used in tampon manufacture such as, but not limited to, sanitary napkins, panty liners, incontinence diapers for babies and adults, bandages and the like, which also incorporates the same well known indicators.

1 Claim, 5 Drawing Sheets

| Index | pH Range | Condition |
|-------|----------|-----------|
| N | 3.8 / 4.2 | Normal Physiologic Vaginal |
| A | 4.5 / 5.0 | Trichomonas (Bacterial Vaginosis) |
| B | 5.0 / 6.0 | Gardnerella |
| C | 6.0 / 7.0 | Trichomoniasis (STD) |
| D | 5.0 / 7.0 | T. Vaginalis |
| E | 4.5 / 7.0 | Primary Vaginal Infections |

FIG. 8B

INDICATOR TAMPON APPLICATOR

This application is a continuation-part-of U.S. Pat. No. 08/477,401, filed Jun. 7, 1995 now abandoned.

CROSS REFERENCE OF A RELATED PATENT

This application is an improvement over our U.S. Pat. No. 5,273,521 issued 28 Dec. 1993 and entitled Tampon Applicator for Delivery of A Medicament, which discloses a tampon delivery applicator that is designed to deliver medicaments via a tampon body mounted on a wand which does not allow for testing the biological fluid prior to applying medicament, nor does it allow for an accurate means of measuring the dosage of medicament administered.

BACKGROUND OF THE INVENTION

I. Field of Invention

The present invention relates to tampons, more specifically to an improved tampon assembly or tampon applicator incorporating indicators in the manufacture well known in the medical field for testing excreted biological fluids for comparison to accompanying diagnostic, color chart. Said indicators may also be applied, but not limited to, sanitary napkins, panty liners, incontinence diapers for babies and adults, bandages and the like that utilize the same or similar hydrophilic materials for absorbing biological fluids as that of a conventional tampon body.

II. Description of the Prior Art

Conventional tampons for absorbing catamenia, or impregnated with various spermicides, deodorants, etc. are well known in the art as are tampons utilized to carry medicaments into the vaginal cavity. However, a tampon for testing biological fluids which incorporate indicators such as, but not limited to litmus for determining pH balance and identifying other than normal bacterial activity in the biological fluid excreted from the vaginal cavity are virtually unknown in the art as described herein.

Tampons utilized to carry a medicament into the vaginal cavity are well known, and are illustrated, for example, in U.S. Pat. No. 4,309,997, issued Jan. 12, 1982; and U.S. Pat. No. 4,318,405 and various other patents described therein. All tampons have in common the use of an absorbent material, generally referred to as hydrophilic. In addition to aforementioned patents, hydrophilic materials are described in, inter alia, U.S. Pat. No. 4,475,911, issued Oct. 9, 1984. As used herein, the term "absorbent" refers to materials which are hydrophilic as that term used in U.S. Pat. No. 4,475,911.

As the foregoing patents demonstrate, it is well known to use various "medicaments," which, as used herein, includes materials such as deodorants and the like as well as material whose use is more generally considered to be for therapeutic purposes. Medicaments may be used seriatim in conjunction with tampons, that is, the medicament is inserted into the vaginal cavity, followed by the tampon to prevent leakage. Such a seriatim procedure has numerous obvious disadvantages. Attempts to avoid these disadvantages generally fall into two categories, either the tampon is impregnated with the medicament, such as is described in U.S. Pat. No. 4,309,997, or the medicament is carried in encapsulated form by the tampon, as is described in U.S. Pat. No. 4,318,405. Devices of the type described in U.S. Pat. No. 4,309,997 present problems related to the shelf life of the medicament, allergic reactions to the type of medicament used, and the inconvenience of pre-wetting the tampon, which is often required. Tampons of the type described in U.S. Pat. No. 4,318,405 retain the encapsulated medicament in the tampon both before and after insertion of the tampon into the vaginal cavity, and so may suffer from many of the same disadvantages as the impregnated tampons. In addition, upon dissolving of the encapsulated medicament, much of the medicament will be absorbed by the tampon itself, rather than being applied directly to the body surfaces. Because of the relatively small volume of medicament carried in such a device, often the medicament fails to reach the affected area in sufficient strength. There is also a possibility that the vaginal cavity may be lacking in a sufficient amount of body fluid to dissolve the capsule and ensure medicament application.

Insofar, the prior art which incorporates use of medicaments do not identify or make known a process for identifying whether or not bacterial condition of the vaginal cavity is conducive to introduction of such medicaments, therapeutic or contraceptive. Within this description of the prior art, reference to indicators identifying pH levels are intended as an example for illustrative purposes but not for its use to be limited by such example.

Extensive research in the field of Gynecology confirms that the vaginal cavity contains numerous naturally occurring bacterial flora which are very sensitive to the introduction of medicaments. The condition of the flora is generally identified by toxicity and can be measured via a pH test process well known in the medical field. As previously mentioned, a tampon or other hydrophilic material utilized for absorbing and testing of biological fluids incorporating in the manufacture an indicator such as litmus, for determining pH balance of biological fluid excreted from the vaginal cavity or such as keytone for testing excretions from the adjacent urethral opening are currently unknown in the art. This example of an indicator applied to test pH generally uses, but is not limited to litmus, also known as turnsole or lacmus, which contain litmus, a natural pigment obtained from lichens whose main principle is azolitmin manufactured primarily in a paperlike form whereby color-indicators range from acidic pH colored red (below 4.5) to alkaline pH colored blue (above 8.3). Azolitmin is a brownish-red coloring principle found in cudbear and other commercial litmus preparations for testing. Cudbear is a dusky-red-purple to very dusky red powder obtained from species of *Rocella de candolle, Lecanora archius* or other lichens. Amaranth is another commonly used herb that is a red azo dye used in place of cudbear preparations. There are no known toxic exposures to the agents constituent in litmus, its variations or principle components. Rather, litmus detects toxicity variations present in biological fluids indicative of other than normal conditions. Normal pH levels within the vaginal cavity range approximately from 3.8–4.2. When the vaginal pH is 5.0 or greater, levels indicate vaginosis or atrophic vaginal discharge as described in *Principles and Practice of Clinical Gynecology*, p. 598. Utilizing such tests provides a means for early detection of harmful bacterial activity which cause infections that could be identified via corresponding pH levels at an early and treatable stage. Due to the nature of the indicator, application is not harmful to the user nor is it chemically reactive to present medicaments.

The only relevant prior art discovered is identified in an article referencing tests conducted at the University of Athens entitled "*Evaluation of Lactate Dehydrogenase Activity as an Index of Cervical Malignancy*" (European Journal of Gynaecology Oncology, 12(6) 471–6 1991); presents a tampon known as Gynaegnost coated with chemical compounds PMS (phenazin methosulfate) basically an electron conductor which draws NADH (biological fluid) to the surface cover of the tampon coated with NBT (nitrobluetetrazolium-chloride), a coloring agent which becomes blue (diformizan) in the presence of LDH (lactose dehydrogenase) activity. Intensity of the diformizan coloration corresponds to the intensity of the LDH activity. Several disadvantages are apparent with this method:

a. A lay user could conduct this test outside a laboratory setting, however, results are intended to identify pre-invasive or invasive cervical malignancy which is a very serious disorder to have a lay user diagnose particularly with one coloring agent and chemical compounds that should be used under the supervison of a gynelogical authority.

b. While Gynaegnost tests for cervical cancer (CaCx), the test results have concluded with many false positive readings which distorts the accuracy and validity of the test.

c. Further notations in the journal specifically state that the test should not be conducted in the presence of vaginitis or cervicitus due to the occurrence of the false positive disqualification.

In contrast, the preferred embodiment of the present invention eliminates such unknowns by simply using the indicator to test the biological fluid and provide a quantitative analysis whereby coloration relates directly to a numerical level of intensity (acid or alkaline) with a corresponding prognosis chart indexed according to infection type that is generally accepted by gynecology professionals for which charts can be amended accordingly with continuous improvement of gynecology standards. As noted, Gynaegnost is not recommended for use during the presence of infection, whereas the present invention conversely encourages use of indicator testing pH balance of biological fluids to identify an impending infection for purposes of preventing progression of a simple infection to cervical malignancy.

The present invention not only utilizes the indicator as a pH test system for other than normal conditions of the vaginal cavity but further for tracking daily pH balance for purposes of natural contraception. There exists in the prior art many patents for tampons previously mentioned which include contraceptives as a form of medicament, in the manufacture. There does not appear to be any known prior art that utilizes the tampon assembly incorporating indicators for contraceptive purposes by determining whether chemical balance is conducive to conception which can therefore be avoided if the user so chooses.

OBJECTS AND ADVANTAGES

The object of the present invention is to provide a simplified tampon applicator test apparatus for use during other than menstrual periods to detect the presence of bacterial activity via internally or externally excreted biological fluids collected within an absorbent or hydrophilic body designed for fluid accumulation and assembly parts previously mentioned which come into contact with said biological fluids by incorporating, color indicators in the manufacture of the tampon assembly, the conventional hydrophilic tampon body, applicator housings, plungers, withdrawal strings or any other part of the tampon assembly that comes into contact with said excreted biological fluids whereby results are interpreted by comparing the resultant color of the tampon assembly wholly or in parts to the accompanying color-corresponding prognosis chart. Within this description of the preferred embodiment, reference to pH indicators are meant as an example for illustrative purposes but not for its use to be limited by such example.

The improvements in the preferred embodiment have numerous obvious advantages:

a. Indicators are available in various material forms such as paper strips, dyes, pastes and the like with varying degrees of color spectrums that can be incorporated in accordance with the manufacture of a tampon assembly, wholly or in parts.

b. The nature of such indicators provides a very safe means of testing that will avoid inflicting harm on the user and is characteristically not chemically-reactive with existing medicaments.

c. The tampon assembly or tampon applicator for delivery with indicators combined provides a test system that is versatile, simple, user-friendly, easy to read and easy to dispose of.

d. False-positive distortion is less likely to occur as indicators are not adversely affected in the presence of infection but rather indicative of the infection.

e. Indicators can be applied to any embodiment utilizing hydrophilic material for absorbing excreted biological fluid as the material which absorbs the fluid is a biological sample sufficient for testing.

f. When indicators are used in conjunction with a tampon applicator for delivery of a medicament, the presence of such indicators will not hinder the application of medicaments but instead would enable testing the effectiveness of said medicaments post-application.

g. The improved rounded front end of tampon applicator for delivery of a medicament would allow for easier insertion of the tampon applicator and make the removable closure more accessible and therefore easier to remove before use.

h. The tampon applicator for delivery of a medicament is further improved by a dual-member telescopic ejection wand means with dosage measurement scale to provide a more efficient and accurate means of medicament application to ensure user applies the proper dosage in accordance with prescribed quantities whereby the dual-member wand precipitates easier handling of the medicament to be applied.

i. The improved dual-member telescoping wand with dosage measurement scale allows medicament to be selectively pre-package or separately package a wider variety of medicaments such those of a lesser density for example, liquids which could prematurely activate collapse of the hollowed bore. This method of selective packaging provides for a more sanitary system of medicament application and prevent exposure of said medicaments to bacteria present in the environment. Further, this improvement would serve to minimize waste even further than is already available.

The preferred embodiment is in the form of a tampon applicator for delivery of a medicament with improved rounded front end, improved wand for use in seriatim procedure incorporating dosage measurement scale for accuracy, an alternative dual telescoping wand assembly which allows for but is not limited to, application of less dense medicaments, selective pre-packaging and provide a more sanitary means of medicament handling prior to insertion. Further includes a conventional tampon assembly, separately or as a whole, incorporating in its manufacture indicators for testing excreted biological fluid. Moreover the method of applying indicators in the manufacture can also be applied, but not limited to, sanitary napkins, panty liners, incontinence diapers for babies and adults, bandages and any other such hydrophilic materials utilized for absorbing excreted biological fluids.

SUMMARY OF THE PRESENT INVENTION

According to the present invention, a tampon assembly adapted for carrying a medicament for selective expulsion during use has an improved tubular inserter incorporating a dosage measurement scale, a dual telescopic tubular inserter means consisting of the principle tubular member, wherein the lead end is open with a sealable closure which slidably engages a secondary telescoping member fitted and closed at the abutting end, of which one or both tubular members incorporate dosage measurement scale such as a milligram scale, on which an improved elongated tampon body with improved rounded front end and applied thereto is mounted by means of an axial bore extending through the body so as to slidably engage the exterior of the primary member of the improved inserter having an open end sealable with a closure, on which the tampon body being with rounded front end is comprised of an absorbent material so as to have a porous outer surface formed in the shape of a radially-disposed longitudinal pleats wherewithin or whereon the indicators may be applied and a porous inner surface formed by the bore, with improved string means also incorporating indicators, attach to the body portion for use in removing the tampon body after use. A medicament, preferably in a solid, gelatin, ointment, foam, paste or encapsulated form, is disposed in the remainder of the bore so as to abut the inserter closed end, or can be contained within the improved inserter primary member whereby secondary member is telescopically fitted and the retraction of the secondary member would allow a space within the primary member for medicament to be placed or selectively pre-packaged accordingly with dosage measurement scale, secondary member would be telescopically replaced to abut the contained medicament. The normally closed end of primary member of inserter has an improved open end sealable with a closure to contain medicament prior to use whereby, telescopic injection of secondary member within the primary member will eject medicament from dual-member wand primary member when closure is removed prior to insertion and is selectively expelled via the primary member by longitudinal relative movement between primary and secondary members of the inserter within the bore of the tampon body portion. In the preferred embodiment, a peripheral ring and grip is formed on rear end of the inserter primary member to serve as a platform for tampon body prior to insertion and a second peripheral ring appears on the secondary member opposite the end abutting the medicament to engage the primary member peripheral ring to insure selective expulsion of the medicament contained within the primary member and to further insure smooth longitudinal relative movement without premature collapse of said bore. Moreover, application of indicators to a conventional tampon assembly consists of a hydrophilic tampon body, applicator housings, plungers, withdrawal strings, etc. are so simultaneously improved by application of said indicators constituent to the preferred embodiment.

BRIEF DESCRIPTIONS OF THE DRAWINGS

The present invention may be more readily understood by referring to the accompanying drawing, in which.

DETAILED DESCRIPTION OF THE PREFERRED EMBODIMENT

Figures 1, 2:
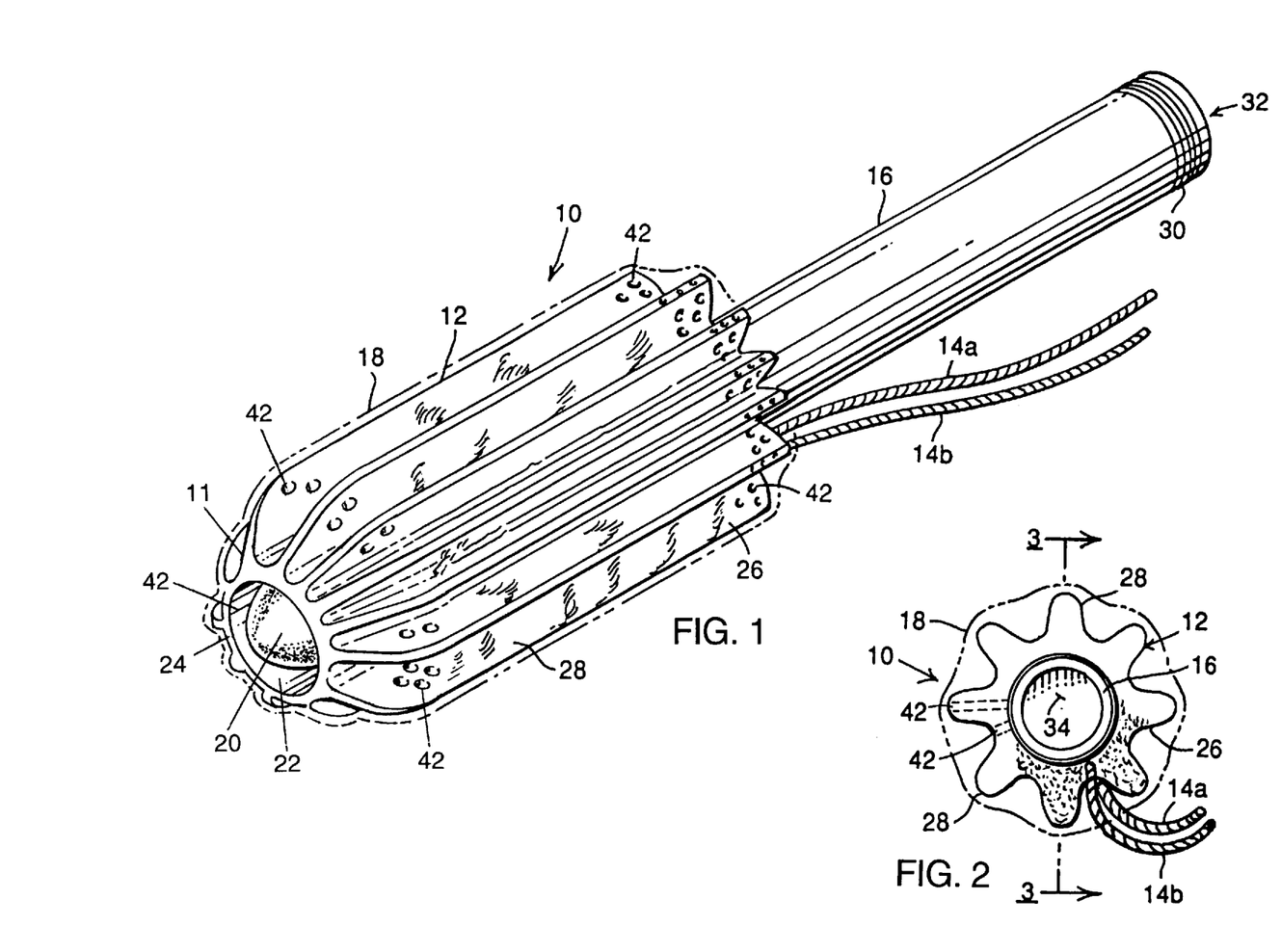
FIG. 1, is a perspective view of a tampon body delivery assembly with the conically rounded front end and measurement scale on the wand which abuts the tampon body at the closed end for seriatim insertion according to the present invention.
FIG. 2, is a wand end view of a tampon delivery assembly with the conically rounded front end shown.
Figure 3:
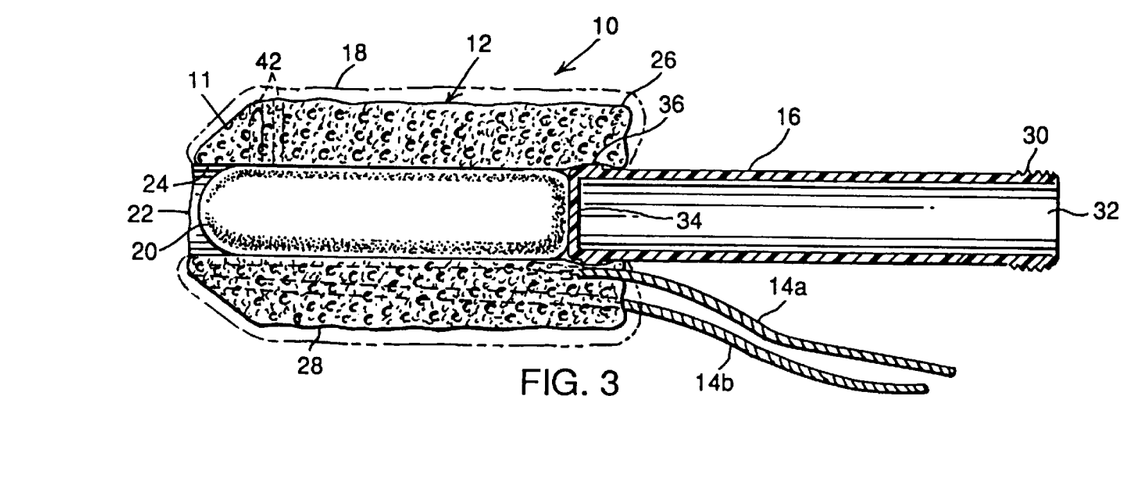
FIG. 3, is a cross-sectional view taken on line 3—3 of FIG. 2.

Referring now to the FIGS. 1 through 3, there is shown a tampon assembly 10 with a conically rounded front end 11 according to the present invention, which further consists of a tampon body 12, a withdrawal string 14a, 14b, and a wand or inserter 16 with medicament measurement dosage scale 5 1. Preferably, the tampon body 12 with its improved conically rounded front end 11 is enclosed in a removable protective covering, 18, shown in dotted lines in FIGS. 1, 2, 3, 5 and 7, to maintain the cleanliness of the tampon body 12 with improved conically rounded front end 11 prior to use. A medicament 20 is disposed in a longitudinal bore 22 extending through the tampon body 12 with rounded end 11. The withdrawal string 14 is illustrated as being configured in a "U", so that one end 14a extends through the bore 22 and the other end 14b extends along the external surface of the tampon body portion 12 with rounded front end 11.

The tampon body 12 with improved rounded front end 11 is formed of an absorbent material, as that term has been previously defined, so that the bore, 22, forms a porous interior surface 24. The tampon body 12 with the improved front end 11 has a porous outer surface 26 in the form of a series of longitudinally aligned, (see FIG. 1), and radially-extending, circumferentially-disposed pleats (see FIG. 2).

The wand or inserter 16 has a grip 30 formed at one end thereof. As is shown in FIG. 3, the wand 16 with dosage measurement scale 51, has an open end 32 adjacent the grip 30 and a closed end 34, which abuts the encapsulated medicament 20. A peripheral ring 31 is formed on the wand 16 with dosage measurement scale 51 adjacent the closed end 34 so as to directly engage the porous inner surface 24 of the tampon body portion 16 at the bore 22 to scrape the interior of the bore 22 as the medicament 20 is ejected from the tampon body 12 with rounded front end 11, as will be described herein after, in addition to providing a seal of the bore 22 until final withdrawal of the wand 16 with dosage measurement scale 51 from the tampon body portion 12 with rounded front end 11.

Figure 4:
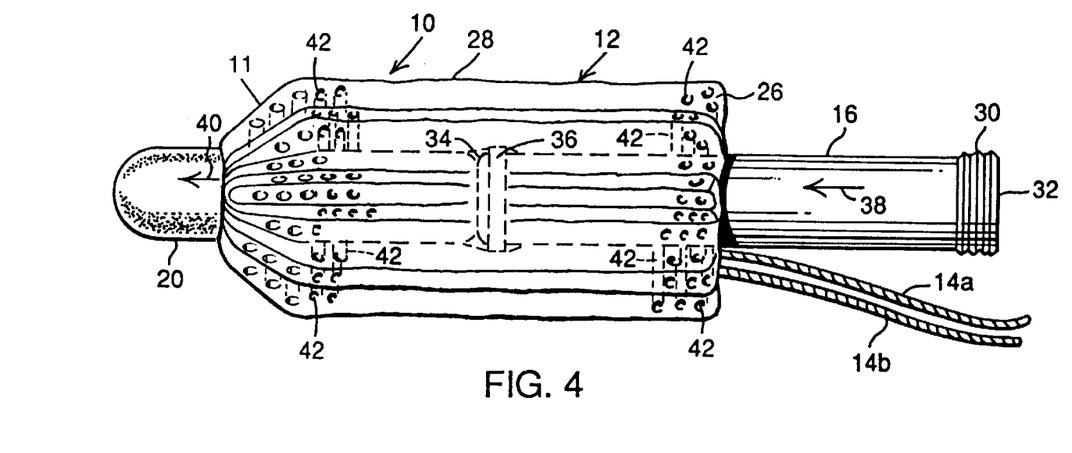
FIG. 4, is a side view of the tampon delivery body with the conically rounded front end and dosage measurement scale on the wand which abuts the medicament in a seriatim procedure at the closed end of the present invention of FIG. 1, illustrating the ejection of a medicament from the tampon delivery body assembly, with the conically rounded front end.

Referring now to FIG. 4, the tampon assembly 10 is shown in a disposition in which the medicament 20 is in the process of being expelled from the tampon body 12 with rounded front end 11. For purposes of ease of understanding of the operation of the tampon assembly 10, the insertion of the tampon assembly 10 into the vaginal cavity has not been shown. Such insertion is performed in the conventional manner. Specifically, the process would include the removal of the removable protective covering 18 from the tampon body 12 with rounded front end 11 or tampon assembly 10, the insertion of the medicament 20 into the bore 22 if not already inserted, the insertion of the wand 16 with dosage measurement scale 51 into the bore 22 either prior to or subsequent to insertion of the medicament 20 thereunto, and the insertion of the tampon assembly 10, so assembled, into the vaginal cavity with the ends of the withdrawal string 14 remaining outside the vaginal cavity. As is indicated by the arrow 38, the wand 16 is moved so that the closed end 34 passes along the bore 22, thus moving the medicament 20 out of the bore 22, as is indicated by the arrow 40. At such time as the medicament 20 is completely expelled from the bore 22, the movement of the wand 16 with dosage measurement scale 51 in the direction shown by the arrow 38 is terminated, and the wand 16 with dosage measurement scale 51 then moved in the opposite direction to the movement shown by arrow 38, until the wand is completely withdrawn from the tampon body and is then further withdrawn from the vaginal cavity. Thus, upon expulsion of the medicament 20 from the tampon body 12 with rounded front end 11 as above described, and the withdrawal of the wand 16 with dosage measurement scale 51 from the tampon body 12 with rounded front end 11 and the vaginal cavity, the medicament 20 is dissolved within the vaginal cavity as well as sealing the vaginal cavity to maintain the medicament 20 therewithin.

Figure 5:
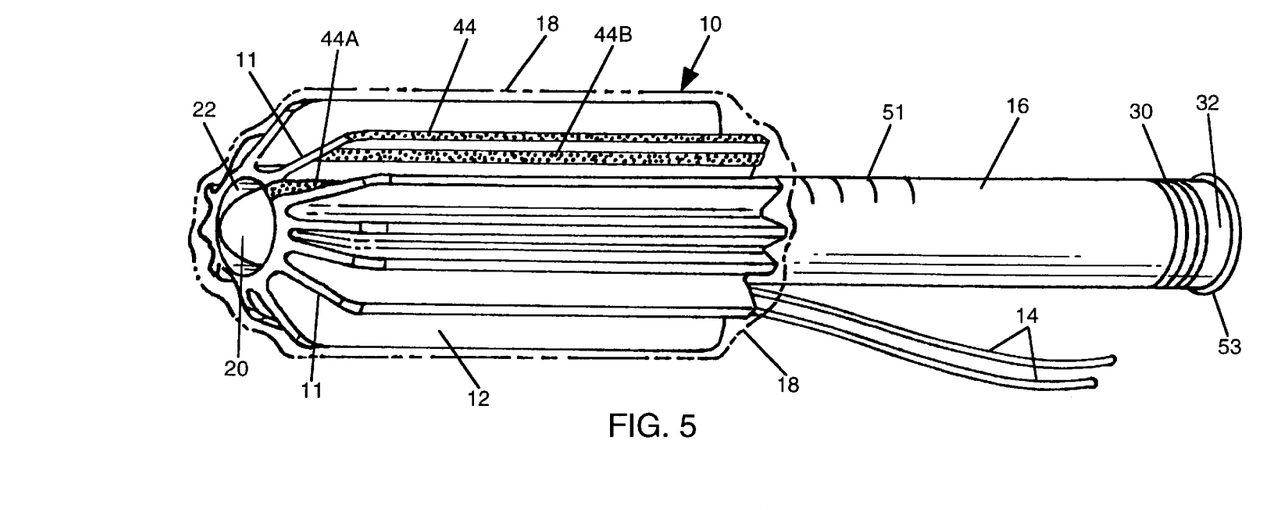
FIG. 5, is a perspective view of a tampon delivery body with indicators in example of using but not limited to, paper and shown in various positions as an example of indicators other than dye or component derivatives applied.

Referring now to FIG. 5, there is shown a tampon assembly 10 with a conically rounded front end 11 according to the present invention, which further consists of a tampon body 12, a withdrawal string 14a, 14b, and a wand or inserter 16 with medicament measurement dosage scale 51 and indicators 44, outer diameter 44A, inner diameter 44B, of side surfaces applied in example as a paperlike form. Preferably, the tampon body 12 with improved conically rounded front end 11 is enclosed in a removable protective covering, 18, shown in dotted lines in FIGS. 1, 2, 3, 5 and 7, to maintain the cleanliness of the tampon body 12 with improved conically rounded front end 11 prior to use. A medicament 20 is disposed in a longitudinal bore 22 extending through the tampon body 12 with rounded front end 11. The withdrawal string 14 is illustrated as being configured in a "U", so that one end 14a extends through the bore 22 and the other end 14b extends along the external surface of the tampon body portion 12 with rounded front end 1 1. The operation of the tampon assembly remains the same as that described in FIG. 4.

Figure 6:
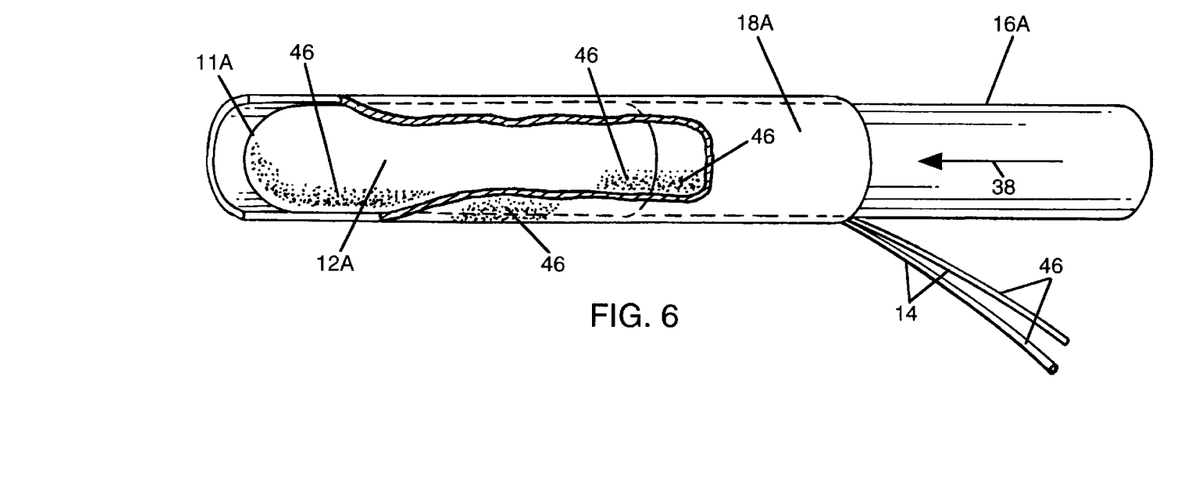
FIG. 6, is a perspective cutaway view of a conventional tampon body assembly with rounded front end showing various areas with a variation of indicators in example of using a dye or component derivative other than paper applied.

Referring now to FIG. 6, a cutaway perspective view is shown as an example showing a conventional tampon body assembly with rounded front end 11A which further consists of a tampon body 12A, a withdrawal string 14 and an external applicator housing 18A including an applicator plunger 16A conventionally manufactured of cardboard or injection molded plastic which ejects the tampon body 12A via the applicator housing 1 8A in the direction of arrow 38 which slidably engages the plunger 16A for ease of insertion into the vaginal cavity. Indicators 46, shown are applied in example of using an indicator dye or derivative component 46 rather than a paperlike indicator as applied to the tampon assembly, wholly or in parts, consisting of the tampon body 12A, applicator housing 18A, plunger 16A and withdrawal string 14.

Figure 7:
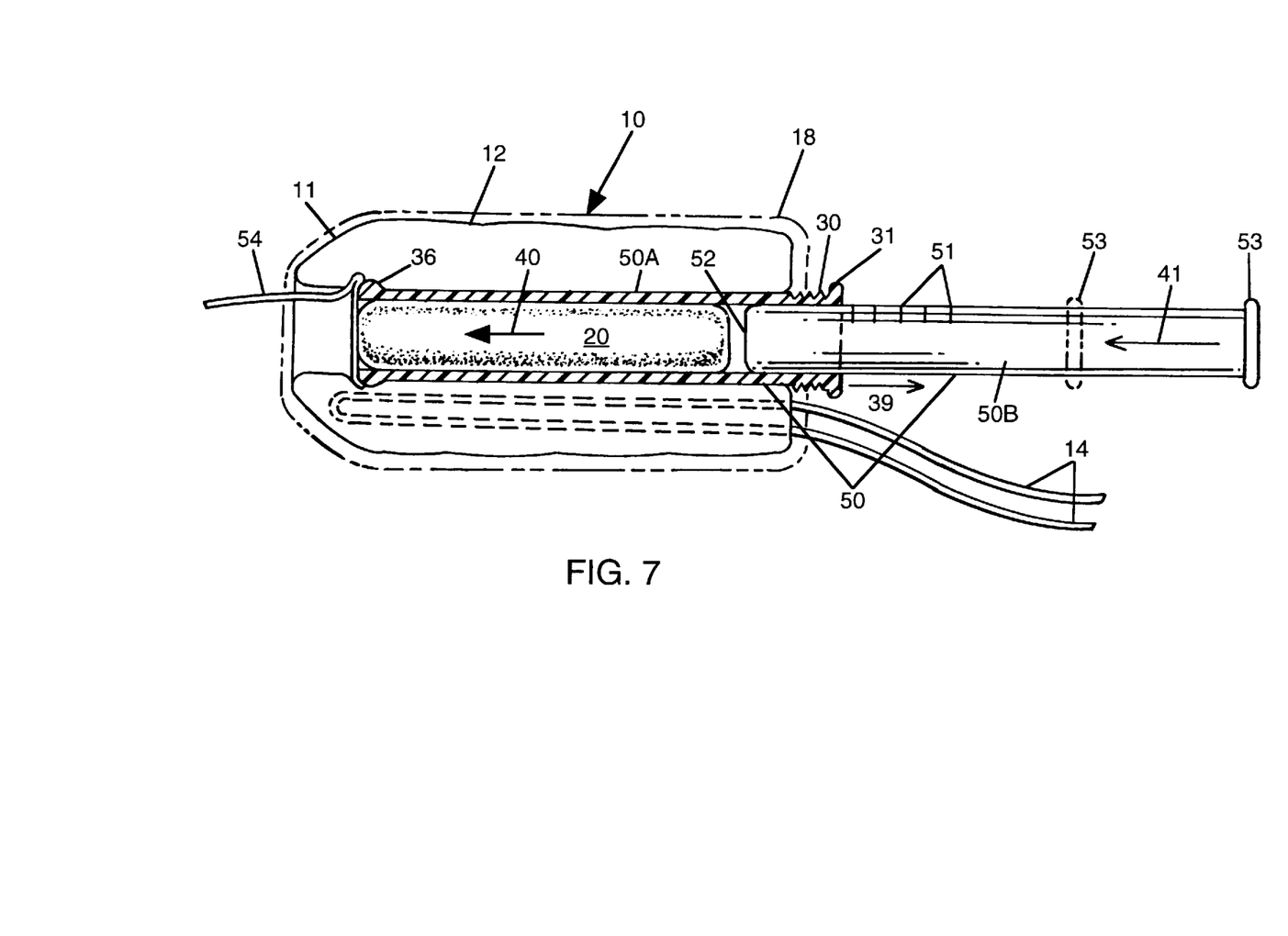
FIG. 7, is a cross-sectional view of a tampon delivery assembly with improved dual telescopic plunger members with an open end sealable on the lead end of the primary member with a closure, a secondary member telescopically fitted incorporating dosage measurement scale on either member with applicable set of peripheral rings.

Referring now to FIG. 7, a sectional view of a tampon assembly 10 with tampon body 12 and rounded front end 11 is enclosed in a removable protective covering 18 whereby tampon assembly 10 contains an improved telescopic medicament plunger 50 consisting of primary member 50A and secondary member 50B with dosage measurement scale 51 present on either member telescopically fitted whereby secondary member 50B is directionally retractable indicated by arrow 39 wherewithin primary member 50A medicament 20 is pre-disposed and secondary member 50B slidably reengages primary member 50A in a longitudinal relative movement 41 so as to abut at the closed end 52 with the medicament 20 whereby open end 36 with removable seal 54 is removed and secondary member 50B continues longitudinal movement indicated by arrow 41 ejecting medicament 20 as indicated by arrow 40 out the inserter unsealed end 36 when primary member 50A with peripheral ring 31 and grip 30 fully engages secondary member 50B with peripheral ring 53 and the entire plunger assembly 50 can be removed by repeating retraction direction 39 when peripheral rings 31 and 53 abut. The tampon body 12 will remain disposed within the vaginal cavity awaiting selective retraction via withdrawal string means 14.

Figure 8A:
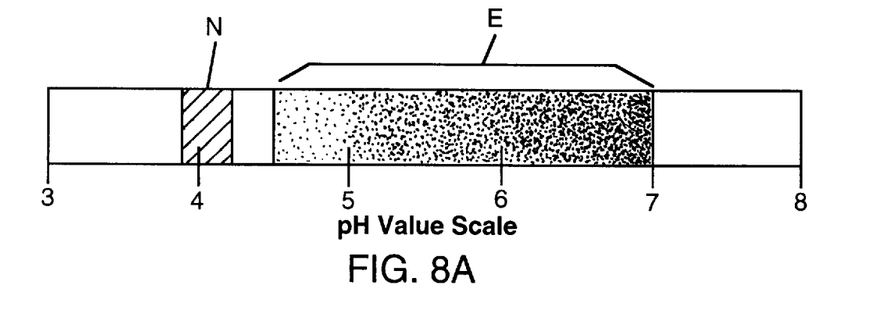
FIGS. 8A and 8B show a chart-graph for comparison of resultant color change of indicator displaying the indexed range of such applied example indicator, FIG. 5 and FIG. 6, such example identifying an applicable range of pH values present in a normal physiologic vaginal environment versus active primary infections of the vaginal cavity.
Figure 8B:
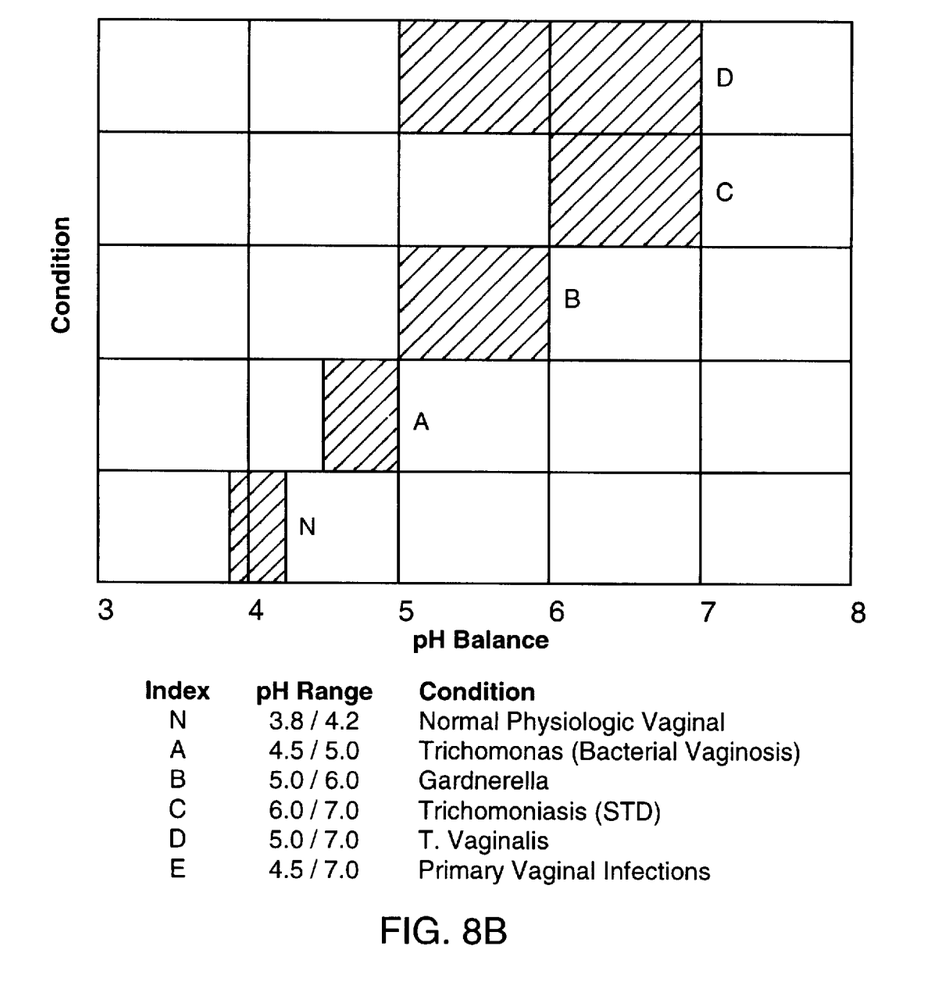

Referring now to FIG. 8, Heretofore, indicators have been identified as having a corresponding prognosis chart and a pH indicator is used to provide the most concise example for purposes of illustration such as this chart provides. Indicators in many variations correspond to many different prognosis scales and this example chart corresponds to a pH scale indicative of infections which correspond directly to the resultant color change in the indicator as applied to the tampon assembly wholly or in parts fir such example purpose of determining pH.

In the preferred embodiment, the tampon body 12 with rounded front end 11 has a plurality of randomly-disposed perforations 42 extending between the outer surface 26 and the and the bore 22 along the length thereof. In FIGS. 1 and 4, only the perforations 42 adjacent the ends of the tampon body are illustrated, it being understood that the use of the perforations 42 is not limited to only those locations illustrated in FIGS. 1 and 4, but preferably extend along the length of the tampon body 12 with rounded front end 11. The use of the perforations 42 is particularly preferred when it is desirable to have the medicament 20 be absorbed into the tampon body 12 after expulsion therefrom, so as to act in a manner similar to an internal bandage in applying the medicament within the vaginal cavity. Application of indicators 44, 44A, 44B and 46 do not hinder affectation of said perforations as described above but rather are incorporated in the manufacture.

In the preferred embodiment shown, the wand 16 and dual member wand 50 incorporates dosage measurement scale 51 in either embodiment. Wand 16 utilize peripheral ring 31 in a seriatim procedure in order to compress that portion of the porous interior surface 24 of the tampon body 12 as the ring 31 moves along the bore 22. Wand 50, primary member 50A, utilizes open front end 32 with sealable closure 54 to allow pre-disposal of medicament, on secondary member SOB peripheral ring 53 engages primary member 50A abutting medicament 20 prior insertion of medicament. If desired, in wand 16, in order to avoid the peripheral ring 31 passing out of the bore 22 at the time the medicament 20 is expelled therefrom, with the possibility that the ring 31 would then be readily withdrawable into the bore 22 to permit the withdrawal of the wand 16 from the tampon body 12 with rounded front end 11. The length of the withdrawal string 14 may be adjusted to provide guidance to the user as to the proper length of movement of the wands 16 or 50 into the bore 22. The string 14 may also be held by the user during the movement of the wands 16 or 50 through the bore 22 in order to assist in the initiation and continuation of the relative movement of the wands 16 or 50 with respect to the tampon body 12 with rounded front end 11 as indicated by the arrows 38 and 40. Various other methods are utilized if so desired, in order to avoid the passage of the peripheral rings 31 and 53 out of the bore 22 at the time of expulsion of the medicament 20 therefrom. For example, a flange could be formed on the wands 16 or 50 at the appropriate longitudinal point so as to engage the tampon body 12 to terminate relative movement between the wands 16 and 50 and the tampon body 12 at the point of expulsion of the medicament 20 from the bore 22 and rounded front end 11.

From the foregoing description, it will be apparent that the present invention may be distributed in any one of at least three forms. For example, the tampon assembly 10 with rounded front end 11 may be distributed as shown in FIG. 1 and FIG. 5, with the medicament 20 already inserted. Alternatively, the tampon body 12 with rounded front end 11 and wand 16 with dosage measurement scale 51 applied may be distributed without the medicament, which then is inserted in the bore 22 directly or into wand 50, primary member 50A with removable closure 54 by the user immediately prior to use, thereby avoiding a shelf life problem and sanitary handling with respect to the medicament. In addition, the tampon body 12 with rounded front end 11 and indicators 44, 44A, 44B and 46 applied to the tampon body, housings, plungers, withdrawal string, etc. may be packaged separately from the wands 16 and 50, since the wand 16 may be reused or wand 50 may be prepackaged. In addition, an improved conventional tampon assembly for strictly catamenia absorbing purposes may incorporate indicators 44, 44A, 44B and 46 for use during other than menstrual periods as a test apparatus. In such an embodiment, a number of tampon bodies 12 incorporating indicators 44, 44A, 44B and 46 with rounded front ends 11 may be used over a period of time with a single wand 16 with dosage measurement scale 51 or dual-member wand 50 also incorporating dosage measurement scale 51, thereby further reducing both the cost to the user and the shipping weight and storage volume required. Further, in such an embodiment, the user will experience minimal waste, expedient application, dosage accuracy and immediate diagnostic results delivered in a sanitary manner.

The present invention relates to the structures described above and hereinafter claimed with respect to the tampon assembly 10 and the components thereof, and not to any particular materials of construction. The term absorbent, as used herein, as stated above, comprehends the use of any hydrophilic material. The wands 16 and 50 may be made of any appropriate material such as nontoxic lightweight moldable plastic and may include a dosage measurement scale as applied in the preferred embodiment through methods such as, but not limited to, heat stamping, or incorporating raised numerals during the molding. While it is tubular in the preferred embodiment for purposes of economy of weight and material, the wand 16 or secondary member 50B may be solid if desired or may consist, for example, of a rod with an expanded head functioning as the equivalent of the closed end 34. The material of the removable closure for primary member 50A is conventional and in the preferred embodiment can be constructed of a biodegradable material formed in the shape of the open end and able to be pulled or pushed out. The material of the string is conventional, and therefore the term "string," and the other terms used herein, unless otherwise defined herein, are not limited to the precise materials or depictions contained herein, but rather include structures and materials within the permissible range thereto. The removable protective covering 18 and 18A is also of conventional material, such as paper or plastic film. The covers 18 and 18A may completely enclose the entire tampon assembly 10, as when the medicament 20 is included in the device as distributed.. Obviously, the tampon bodies 12 and 12A with indicators 44, 44A, 44B, 46 and medicament 20 can be packaged separately from the wands 16 or 50, or the tampon bodies 12 or 12A with indicators 44, 44A, 44B, 46 and the wands 16 and 50 can be packaged separately from the medicament 20, or the tampon bodies 12 and 12A with indicators 44, 44A, 44B, 46 can be packaged separately from the medicament 20 and the wands 16 and 50. Consequently, in FIGS. 1, 2, 3, 5 and 7 the tampon body 12 or 12A is shown as enclosed by the protective covering 18 or 18A for purposes of illustration only, and not as a limitation.

The invention claimed is:

1. A tampon applicator comprising;

a housing member capable of holding an insertable member;

said housing member supporting at least one pH indicator, wherein said pH indicator would come into direct contact with a body fluid upon insertion of the applicator into an individual and provide an instant pH reading upon removal of the applicator.

* * * * *